(12) United States Patent
Xi et al.

(10) Patent No.: US 10,702,055 B2
(45) Date of Patent: Jul. 7, 2020

(54) LIGHT EMITTING ORAL CARE IMPLEMENT

(71) Applicant: Colgate-Palmolive Company, New York, NY (US)

(72) Inventors: Wen Jin Xi, Shanghai (CN); Guang Sheng Guo, Yangzhou (CN); Bo Zhang, Yangzhou (CN); Fan Gang Xie, Shanghai (CN); Jian Rong Zhou, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 208 days.

(21) Appl. No.: 16/066,753

(22) PCT Filed: Dec. 22, 2016

(86) PCT No.: PCT/US2016/068262
§ 371 (c)(1),
(2) Date: Jun. 28, 2018

(87) PCT Pub. No.: WO2017/116971
PCT Pub. Date: Jul. 6, 2017

(65) Prior Publication Data
US 2019/0014901 A1 Jan. 17, 2019

(30) Foreign Application Priority Data
Dec. 28, 2015 (CN) .......................... 2015 1 0994741

(51) Int. Cl.
*A46B 15/00* (2006.01)
*A46B 5/00* (2006.01)
(Continued)

(52) U.S. Cl.
CPC ........ *A46B 15/0034* (2013.01); *A46B 5/0095* (2013.01); *A61C 17/222* (2013.01);
(Continued)

(58) Field of Classification Search
CPC ............ A46B 15/0034; A46B 15/0036; A46B 5/0095; A46B 2200/1066; A61C 17/222;
(Continued)

(56) References Cited

U.S. PATENT DOCUMENTS

| 6,026,828 A | 2/2000 | Altshuler |
| 6,029,304 A | 2/2000 | Hulke et al. |

(Continued)

FOREIGN PATENT DOCUMENTS

| BR | 200801042 | 6/2009 |
| CN | 101115527 A | 1/2008 |

(Continued)

OTHER PUBLICATIONS

International Search Report and Written Opinion of the International Searching Authority in International Application No. PCT/US2016/068262, dated May 23, 2017.

*Primary Examiner* — Weilun Lo (57) ABSTRACT

An oral care product array includes a handle component and multiple refill components therefor. The handle component includes a power source. A first refill component includes a first light generating module which emits light in a first spectrum from the first refill component. A second refill component includes a second light generating module which emits light in a second spectrum from the second refill component. Each refill component has a coupled state, when coupled to the handle component, and a decoupled state, when decoupled from the handle component. When the first refill component is in the coupled state, the first light generating module is powered by the power source to emit light in the first spectrum. When the second refill component is in the coupled state, the second light generating module is powered by the power source to emit light in the second spectrum.

13 Claims, 10 Drawing Sheets

(51) Int. Cl.
*A61C 17/22* (2006.01)
*A61N 5/06* (2006.01)

(52) U.S. Cl.
CPC .... *A61N 5/0603* (2013.01); *A46B 2200/1066* (2013.01); *A61N 2005/063* (2013.01); *A61N 2005/0606* (2013.01); *A61N 2005/0644* (2013.01); *A61N 2005/0661* (2013.01); *A61N 2005/0662* (2013.01); *A61N 2005/0667* (2013.01)

(58) Field of Classification Search
CPC .......... A61N 5/0603; A61N 2005/0606; A61N 2005/063; A61N 2005/0644; A61N 2005/0661; A61N 2005/0662; A61N 2005/0667
See application file for complete search history.

(56) References Cited

U.S. PATENT DOCUMENTS

| | | |
|---|---|---|
| 6,616,451 B1 | 9/2003 | Rizolu et al. |
| 6,902,397 B2 | 6/2005 | Farrell et al. |
| 7,223,281 B2 | 5/2007 | Altshuler et al. |
| 7,467,946 B2 | 12/2008 | Rizoiu et al. |
| 8,006,342 B2 | 8/2011 | Nanda |
| 8,186,997 B2 | 5/2012 | Binner et al. |
| 8,314,377 B2 | 11/2012 | Binner |
| 8,429,783 B2 | 4/2013 | Russell et al. |
| 8,984,699 B2 | 3/2015 | Russell et al. |
| 9,198,502 B2 | 12/2015 | Barnes et al. |
| 9,220,583 B2 | 12/2015 | Shani et al. |
| 2006/0194164 A1 | 8/2006 | Altshuler et al. |
| 2008/0131834 A1 | 6/2008 | Shepherd et al. |
| 2008/0256729 A1 | 10/2008 | Link |
| 2009/0083924 A1 | 4/2009 | Shepherd et al. |
| 2009/0271936 A1 | 11/2009 | Walanski et al. |
| 2011/0296643 A1* | 12/2011 | Shepherd ............. A46B 5/0095 15/167.1 |
| 2014/0143963 A1 | 5/2014 | Fattori |
| 2015/0164212 A1 | 6/2015 | Russell et al. |
| 2016/0038762 A1* | 2/2016 | Lin ..................... A61N 5/0603 433/29 |
| 2017/0020277 A1* | 1/2017 | Barnes ............... A61C 17/3436 |

FOREIGN PATENT DOCUMENTS

| | | |
|---|---|---|
| CN | 201333107 Y | 10/2009 |
| CN | 202104478 U | 1/2012 |
| CN | 202146048 U | 2/2012 |
| CN | 202425868 U | 9/2012 |
| CN | 202588726 U | 12/2012 |
| CN | 103096833 A | 5/2013 |
| CN | 203121471 U | 8/2013 |
| CN | 203302574 U | 11/2013 |
| CN | 203436256 U | 2/2014 |
| DE | 202004001004 U1 | 3/2005 |
| DE | 202014003540 U1 | 7/2014 |
| KR | 100607583 B1 | 8/2006 |
| KR | 20070010206 A | 1/2007 |
| KR | 20110009089 A | 1/2011 |
| KR | 20110009089 U | 9/2011 |
| KR | 20120052477 A | 5/2012 |
| KR | 101405422 B1 | 3/2014 |
| WO | 1995/010243 | 4/1995 |
| WO | 2002/021970 | 3/2002 |
| WO | 2004/084752 | 10/2004 |
| WO | 2005/122948 | 12/2005 |
| WO | 2009/047669 | 4/2009 |
| WO | 2010/127629 | 11/2010 |

\* cited by examiner

LIGHT EMITTING ORAL CARE IMPLEMENT

BACKGROUND

An oral care implement, such as a toothbrush, is used to clean the teeth by removing plaque and debris from the tooth surfaces. Toothbrushes may also emit light for purposes such as whitening teeth, killing bacteria within the mouth, detecting the presence of bacteria within the mouth, increasing blood circulation for gum therapy, reducing the pain from gum inflammation, among other potential uses. However, oral care implements that are presently available on the market are single purpose implements, in that they are designed to address only one purpose for which a light emitting toothbrush may be useful. Thus, a need exists for an oral care implement that can emit light that is useful for several purposes, and particularly an oral care implement that uses refill heads to provide the multi-purposed use.

BRIEF SUMMARY

The present invention may be directed, in one aspect, to an oral care product having a handle component and one or more refill components configured to emit a selected spectrum of light. Each refill component may be detachably coupled to the handle component of the oral care product. A light emitting module may be included in the handle component or in one or more of the refill components and powered by a power source in the handle component. In embodiments with light emitting modules included in multiple refill components, each refill component may be configured to emit a different spectrum of light. In embodiments with the light emitting module included in the handle component, the emitted spectrum of light may be selected by having different refill components include different light filters or by the light emitting component being configured to enable selection of the emitted spectrum of light.

In one aspect, the invention may be an oral care product array including: a handle component including a power source; a first refill component comprising a first light generating module configured to emit light in a first spectrum from the first refill component; a second refill component including a second light generating module configured to emit light in a second spectrum from the second refill component, the second spectrum being different than the first spectrum; the first refill component alterable between: (1) a decoupled state in which the first refill component is separated from the handle component; and (2) a coupled state in which the first refill component is mounted to the handle component and the first light generating module is powered by the power source to emit light in the first spectrum from the first refill component; and the second refill component alterable between: (1) a decoupled state in which the second refill component is separated from the handle component; and (2) a coupled state in which the second refill component is mounted to the handle component and the second light generating module is powered by the power source to emit light in the second spectrum from the second refill component.

In another aspect, the invention may be an oral care implement including: a handle component including: a gripping section; a power source; and an inductive power circuit operably coupled to the power source; and a toothbrush refill head including: a head portion; a plurality of tooth cleaning elements extending from a front surface of the head portion; a light generating module operably coupled to the power source and configured to generate light across a spectral range; and an inductive element operably coupled to the light generating module; the toothbrush refill head alterable between: (1) a decoupled state in which the toothbrush refill head is separated from the handle component; and (2) a coupled state in which the toothbrush refill head is mounted to the handle component and the inductive element of the toothbrush refill head is inductively coupled to the inductive power circuit of the handle component to supply power from the power source to the light generating module.

In still another aspect, the invention may be an oral care product array including: a handle component including: a power source; and a light generating module operably coupled to the power source and configured to generate light across a spectral range; a first refill component including: a first light guide having a light receiving end and a light emitting end; and a first light filter operatively coupled to the first light guide to spectrally limit light emitted from the emitting end of the first light guide to a first spectrum; and a second refill component including: a second light guide having a light receiving end and a light emitting end; and a second light filter operatively coupled to the second light guide to spectrally limit light emitted from the emitting end of the second light guide to a second spectrum, the second spectrum being different than the first spectrum; wherein the spectral range comprises both the first and second spectrums; the first refill component alterable between: (1) a decoupled state in which the first refill component is separated from the handle component; and (2) a coupled state in which the first refill component is mounted to the handle component and the receiving end of the first light guide receives light generated by the light generating module; and the second refill component alterable between: (1) a decoupled state in which the second refill component is separated from the handle component; and (2) a coupled state in which the second refill component is mounted to the handle component and the receiving end of the second light guide receives light generated by the light generating module.

In yet another aspect, the invention may be an oral care implement including: a handle component including: a gripping section; a power source; a light generating module operably coupled to the power source and configured to generate light across a spectral range; and an actuator operably coupled to the light generating module, the actuator configured to spectrally limit light generated by the light generating module to a selected spectrum within the spectral range; and a refill head including: a head portion; a plurality of tooth cleaning elements extending from a front surface of the head portion; and a light guide having a light receiving end and a light emitting end; the refill head alterable between: (1) a decoupled state in which the refill head is separated from the handle component; and (2) a coupled state in which the refill head is mounted to the handle component and the receiving end of the light guide receives the selected spectrum of light for emission from the refill head.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 1:
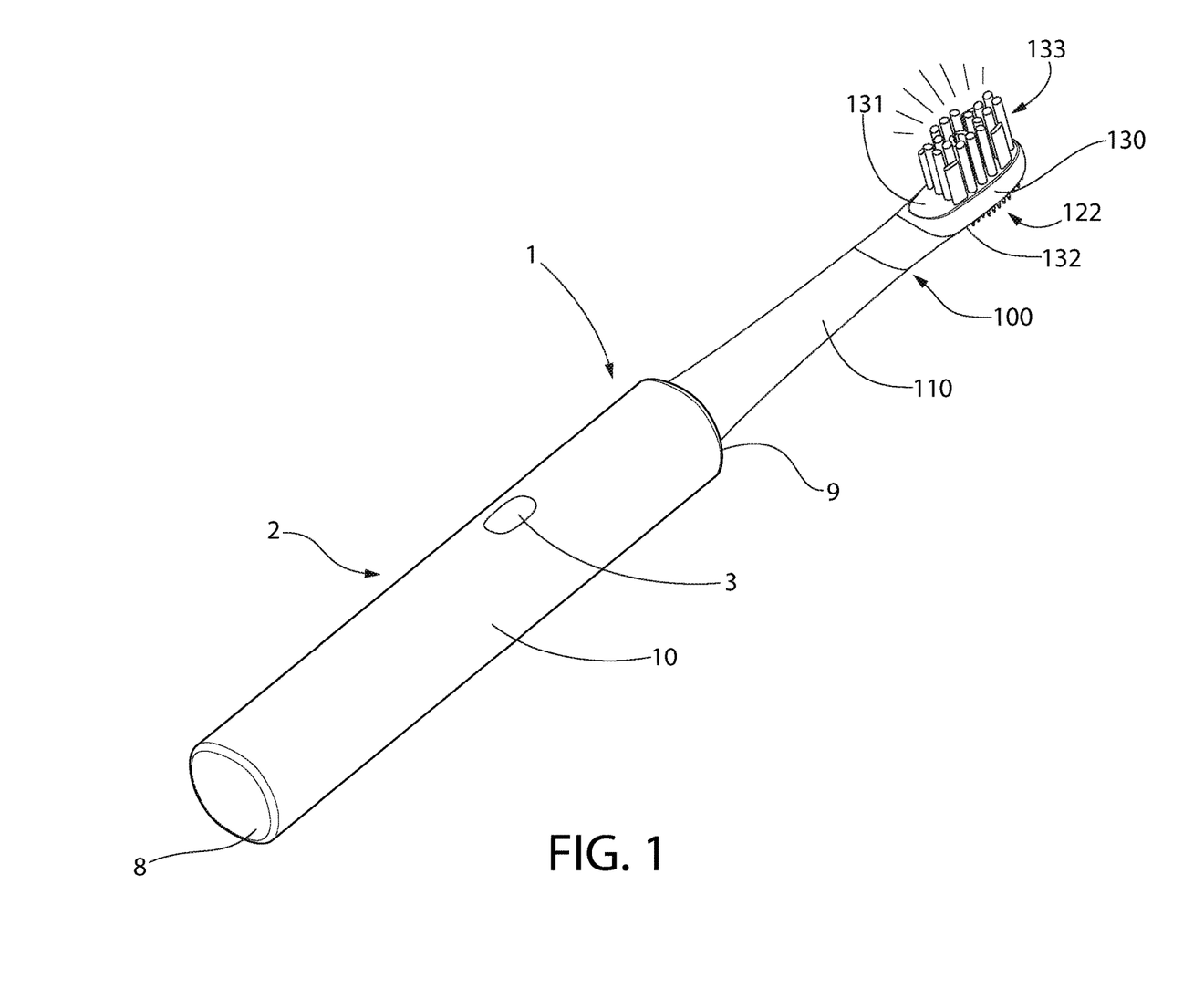
FIG. 1 is perspective view of an oral care implement having a handle component and a refill component in accordance with an embodiment of the present invention.

Turning in detail to the drawings, an oral care implement 1 is illustrated in FIG. 1. In this exemplified embodiment, the oral care implement 1 is an electric or powered toothbrush which emits light from the head. However, the invention is not to be so limited in all embodiments. In certain other embodiments the device may be a manual toothbrush having a replaceable head portion. Thus, the invention is not to be limited to an electric or powered oral care implement 1 unless so limited by the claims.

Figure 2:
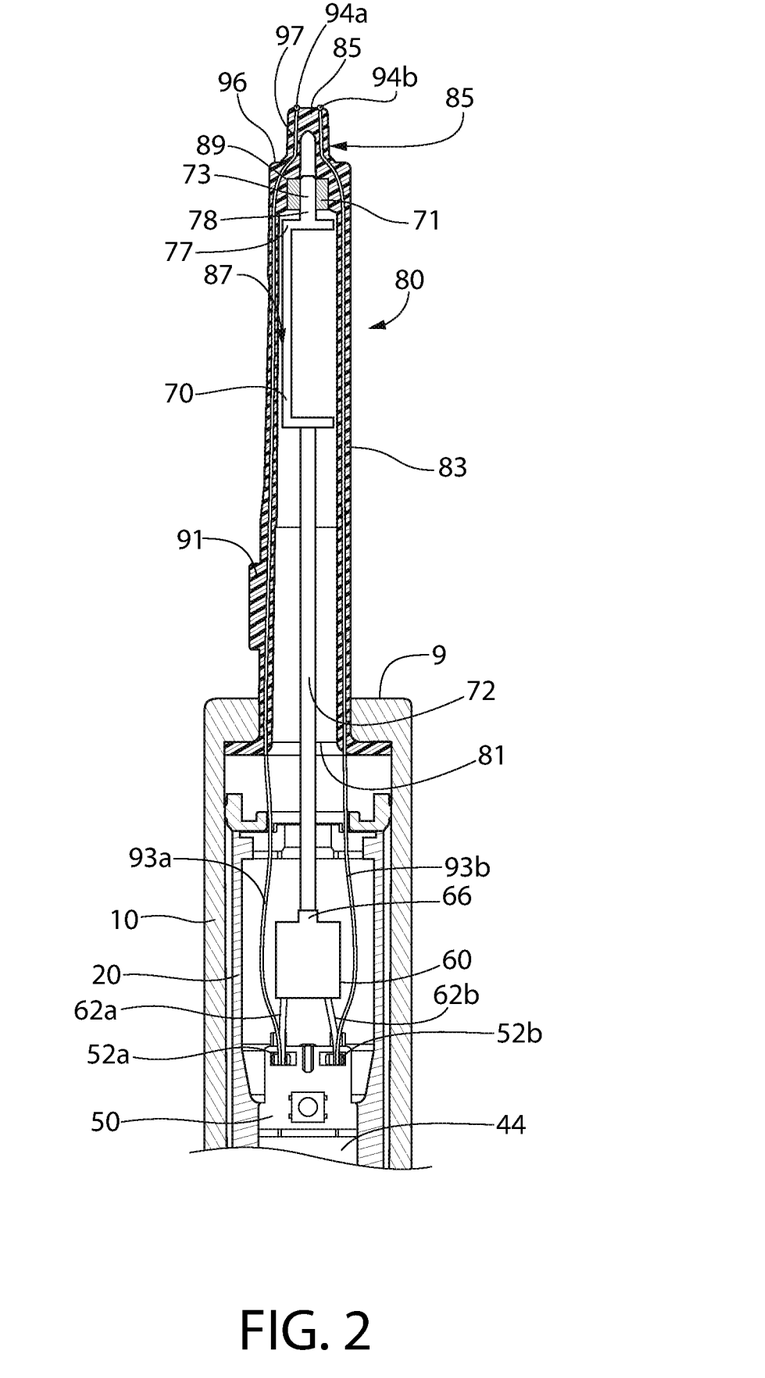
FIG. 2 is a cross-sectional view of a portion of a gripping section and a stem portion of the handle component of the oral care implement of FIG. 1.
Figure 3:
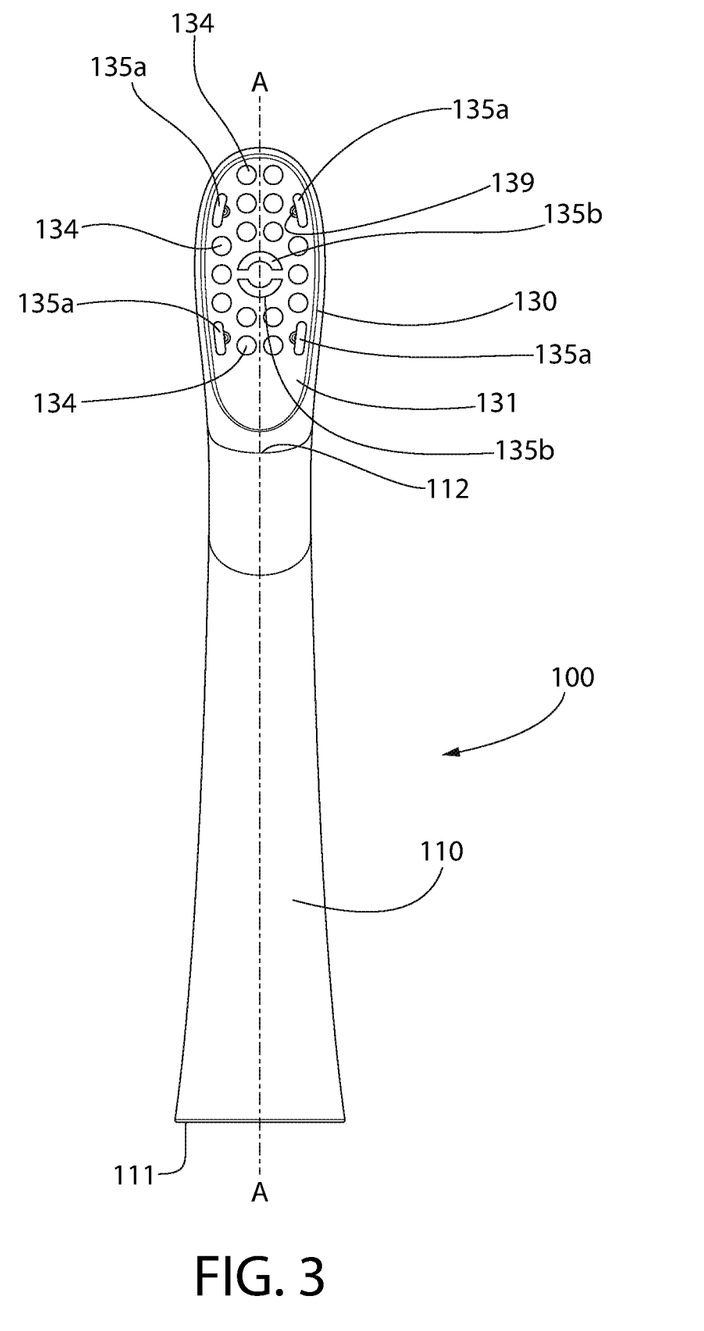
FIG. 3 is a front view of the refill component of the oral care implement of FIG. 1.

With reference to FIGS. 1-3, the oral care implement 1 includes a handle component 2 having a gripping section 10 extending from a proximal end 8 to a distal end 9, a stem portion 80 extending from the distal end 9 of the gripping section 10, and a refill component 100. In the exemplified embodiment the gripping section 10 of the handle component 2 includes an actuator button 3 which serves as a user input device and facilitates powering the oral care implement 1 on and off when the oral care implement 1 is a powered or electric toothbrush. Of course, the actuator button 3 may be positioned at other locations on the handle component 2 than that which is shown in the drawings in other embodiments. In certain embodiments, the actuator button 3 may be replaced by other types of actuator devices. The refill component 100 is detachably coupled to the stem portion 80 of the handle component 2 as described in greater detail below. Different variations of refill components may be used with and coupled to/decoupled from the handle component 2 so that a user has options regarding the type of refill component desired for use.

The refill component 100 includes a sleeve portion 110 and a head portion 130. In certain embodiments, any refill component 100 described herein may be a toothbrush refill head, and as such, a plurality of tooth cleaning elements 133 are mounted to the head portion 130 and extend from a front surface 131 of the head portion 130 of the refill component 100. A soft tissue cleaner 122, which may be formed of an elastomeric material, is coupled to or mounted on a rear surface 132 of the head portion 130 of the refill component 100.

FIG. 2 shows a cross-sectional view of the handle component 2 of the oral care implement 1. The handle component 2 includes the gripping section 10, a chassis 20, a power source 44 (such as a rechargeable battery, a non-rechargeable battery, battery cells, printed batteries, super capacitors, a control circuit that stores electrical energy, or the like), a control circuit 50, a motor 60 having a drive shaft 66, a vibratory source 70, and the stem portion 80. The gripping section 10 is configured to be gripped or grasped by a user to enable the user to manipulate the oral care implement 1 during use. The gripping section 10 also houses the electronic circuitry and components necessary for operation of the oral care implement 1 as a powered or electric toothbrush which emits light. In certain embodiments, the power source 44 may be omitted and the device may be powered by a plug that is coupled to a power supply, such as a wall socket.

The gripping section 10 of the handle component 2 has an interior cavity for accommodating the chassis 20, the power source 44, and the control circuit 50. The interior cavity of the gripping section 10 may be cylindrical in some embodiments although the invention is not to be so limited in all embodiments.

In certain embodiments, the control circuit 50 may include a programmable controller to enable greater functionality and control over the electronic components within the oral care implement 1. The control circuit 50 may be in operable communication with the button 3, thereby enabling a user to provide input to the control circuit 50 for controlling the oral care implement 1. User input to the control circuit 50 may be used to control any one or more of the electrical components included as part of the oral care implement 1.

The stem portion 80 includes an open proximate end 81 which is affixed to the chassis 20 of the gripping section 10 and terminates in a sealed distal end 85. In certain embodiments, the that stem portion 80 and the gripping section 10 may be integrally formed. The body 83 of the stem portion 80 may be tapered and generally cone-shaped, with a smaller cross-sectional profile at the sealed distal end 85 as compared to the open proximate end 81. The external surface of the body 83 of the stem portion 80 may include a coupling element 91 which serves as an orientation key when the refill component 100 is coupled to the handle component 2. In certain embodiments, the coupling element 91 may also serve to lock the refill component 100 onto the handle component 2.

The open proximate end 81 of the stem portion 80 provides a passageway into a stem cavity 87 for receiving and/or retaining the vibratory source 70 and the motor 60 in certain embodiments. The sealed distal end 85 of the stem portion 80 forms an engagement portion 98, which is configured to engage an inner surface of the sleeve portion 110 of the refill component 100 when the refill component 100 is coupled to the handle component 2. The engagement portion 98 includes a stem tip 97 extending from an upper surface 96 of the stem portion 80, such that the upper surface 96 forms an annular transverse shoulder that surrounds the stem tip 97.

The vibratory source 70 includes an extension shaft 72 that may be formed of a synthetic resin and an eccentric shaft 73 that may be formed of metal. The extension shaft 72 of the vibratory source 70 is engaged with the drive shaft 66 of the motor 60 so that the motor 60 can rotate the vibratory source 70 to impart a desired movement to the refill component 100. The motor 60 is electrically connected by 62*a*, 62*b* to the control circuit 50, which controls operation of the motor 60 and is powered by the power source 44. The eccentric shaft 73 of the vibratory source 70 includes an eccentric portion 77 and an axial shaft portion 78. The bottom end of the eccentric portion 77 is connected to the extension shaft 72.

A recessed hole 89 is formed at the end of the stem cavity 87 adjacent the distal end 85 of the stem portion 80. The recessed hole 89 slidably receives the axial shaft portion 78 of the eccentric shaft 73 of the vibratory source 70. Thus, an upper end of the eccentric shaft 73 of the vibratory source 70 is mounted within or adjacent to the stem tip 97. With this configuration, the eccentric portion 77 of the vibratory device 70 is rotatably mounted within the stem cavity 86. The recessed hole 89 serves as a bearing for holding the axial shaft portion 78 of the eccentric shaft 73 of the vibratory source 70. The vibratory source 70 is freely rotated in the stem cavity 86 even under high frequency vibration. In certain embodiments, because the recessed hole 89 serves as the bearing, it is not necessary to provide a separate bearing arrangement for rotatably holding the axial shaft portion 78. Of course, a separate bearing assembly may be provided in some embodiments.

As noted above, the motor 60 is operably coupled to the power source 44 through the control circuit 50. The drive shaft 66 of the motor 60 is operably coupled to the eccentric portion 77 of the vibratory source 70 to rotate the eccentric portion 77 to cause vibrations in the refill component 100, or specifically to the head portion 130 or the tooth cleaning elements 133 thereon. Specifically, when the vibratory source 70 rotates about its axis by the motor 60, the eccentric portion 77 generates a high frequency vibration which is transmitted to the stem arrangement 80 and to the refill component 100 coupled thereto.

Two lead wires 93*a*, 93*b*, which serve to provide power to a light generating module included in the refill component 100, are also coupled to the control circuit 50. These lead wires 93*a*, 93*b* extend from the control circuit 50 to the body 83 of the stem portion 80, and up to the distal end 85 of the stem portion 80, where they each terminate at electrical contacts 94*a*, 94*b*. As depicted, the lead wires 93*a*, 93*b* are embedded within the body 83 of the stem portion 80 to prevent interference with the vibratory source 70. In certain embodiments, the lead wires 93*a*, 93*b* may run along the inside surface of the body 83 of the stem portion 80. In still other embodiments, particularly those without vibratory sources, the lead wires 93*a*, 93*b* may extend within the stem cavity 87 without being embedded within or running along the surface of the body 83 of the stem portion.

Figure 4:
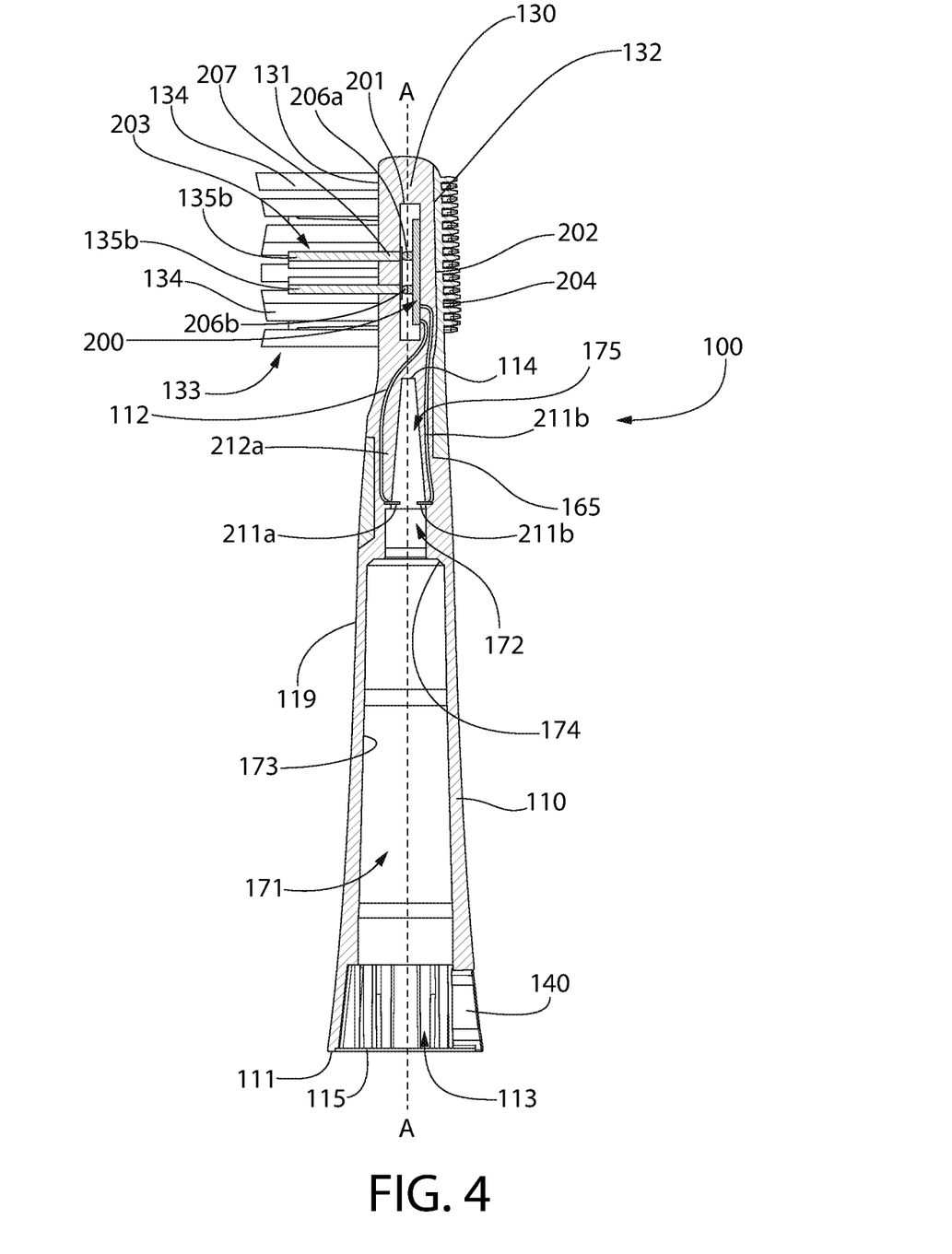
FIG. 4 is a cross-sectional view of the refill component of the oral care implement of FIG. 1.

The refill component 100, shown in FIGS. 3 and 4, includes a sleeve portion 110 and a head portion 130. The sleeve portion 110 of the refill component 100 slides over the stem portion 80 of the handle component 2 to couple the refill component 100 to the stem portion 80. The sleeve portion 110 extends from a proximal end 111 to a distal end 112. In certain embodiments, the head portion 130 and the sleeve portion 110 are formed of a rigid material, such as a rigid plastic material including without limitation polymers and copolymers of ethylene, propylene, butadiene, vinyl compounds and polyesters such as polyethylene terephthalate. The head portion 130 and the sleeve portion 110 may be integrally formed or separately formed and later coupled together. In the exemplified embodiment the head and sleeve portions 110, 130 are integrally formed in an injection molding process.

The head portion 130 of the refill component 100 is located at the distal end 112 of the sleeve portion 110 and includes a front surface 131 and an opposing rear surface 132. As discussed above, there are a plurality of tooth cleaning elements 133 extending from the front surface 131 of the head portion 130 of the refill component 100. The plurality of tooth cleaning elements 133 include a plurality of bristle tufts 134 that are mounted to the head portion 130 and extend from the front surface 131 of the head portion 130. Each of the bristle tufts 134 may include a plurality of bristles. The bristles may be filament bristles, fiber bristles, spiral bristles, nylon bristles, or the like. Each of the above-referenced types of bristles may be end-rounded or tapered. The bristle tufts 134 may be coupled to the head portion 130 using staple technology, anchor-free tufting technologies, or the like as desired.

In addition to the bristle tufts 134, the tooth cleaning elements 133 may include one or more elastomeric tooth contact elements 135*a*, 135*b* extending from the front surface 131 of the head portion 130. In certain embodiments the bristle tufts 134 form a bristle field, and the elastomeric tooth contact elements 135*a*, 135*b* are located within the bristle field. In the exemplified embodiment the bristle tufts 134 extend to a height above the front surface 131 of the head portion 130 of the refill component 100 that is greater than a height that the elastomeric tooth contact elements 135a, 135b extend above the front surface 131 of the head portion 130 of the refill component 100.

In the embodiment shown, the bristle tufts 134 and the elastomeric tooth contact elements 135a, 135b have a specific pattern on the head portion 130 of the refill component 100. However, in other embodiments, other patterns for the bristle tufts 134 and the elastomeric tooth cleaning contact elements 135a, 135b may be used.

In this embodiment, the elastomeric tooth contact elements 135a, 135b include four peripheral contact elements 135a and two central contact elements 135b. The peripheral contact elements 135a include two peripheral contact elements 135a that are transversely aligned near a proximal end of the head portion 130 and two peripheral contact elements 135a that are transversely aligned near a distal end of the head portion 130. The peripheral contact elements 135a are linear wall-like segments having a rib 139 protruding from its inner surface. Thus, the ribs 139 of the peripheral contact elements 135 face inwardly towards a center of the head portion 130.

The two central contact elements 135b are arcuate shaped contact elements positioned centrally on the head portion 130 of the refill component 100. The central contact elements 135b are arranged to form a loop having gaps that are aligned along a plane that extends transverse to the longitudinal axis A-A. The central contact elements 135b have concave surfaces that face one another and convex surfaces facing away from one another and towards the proximal and distal ends of the head portion 130 of the refill component 100, respectively.

The bristle tufts 134 include three peripheral bristle tufts on each opposing side of the head, the three peripheral bristle tufts being positioned between two of the peripheral contact elements 135a in the longitudinal direction of the head portion 130 of the refill component 100. The bristle tufts also include four proximal bristle tufts located between the bottom one of the central contact elements 135b and the proximal end of the head portion 130 and six distal bristle tufts located between the top one of the central contact elements 135b and the proximal end of the head portion 130. The four proximal tufts are positioned generally between two of the peripheral contact elements 135a located near the proximal end of the head portion 130. The six distal proximal tufts are positioned generally between two of the peripheral contact elements 135a located near the distal end of the.

In this exemplary embodiment, the refill component 100 includes a light generating module 200 located within a cavity 201 formed within the head portion 130. The light generating module 200 is configured to emit light in a first spectrum from the refill component 100. To accomplish this, the light generating module 200 includes at least one light source 202, a light guide 203, and a light filter 204. In the embodiment shown, the light generating module 200 includes two light emitting diodes 206a, 206b as the light source 202. Each light emitting diode 206a, 206b is positioned within the cavity 201 to direct light into one of the elastomeric tooth cleaning contacts elements 135b, both of which serve as part of the light guide 203 for the light generating module 200. As part of the light guide 203, the elastomeric tooth cleaning contacts elements 135b form part of a light receiving end 207 of the light guide 203, which is located closest to the light emitting diodes 206a, 206b, and form part of a light emitting end 208, which is distal from the front surface 131 of the head portion 130. Light generated by the light emitting diodes 206a, 206b is received into the light receiving end 207 of the light guide 203 formed by the elastomeric tooth cleaning contacts elements 135b, and the received light is guided down the length of each elastomeric tooth cleaning contacts elements 135b to be emitted at the light emitting end 208 of the light guide 203, which is at the distal ends of the elastomeric tooth cleaning contacts elements 135b. In this manner, light generated by the light source 202 is emitted from the refill component 100. Although the above describes light as being emitted from the front surface 131 of the head portion 130 and/or from the elastomeric tooth cleaning contacts elements 135b, in certain embodiments, light may be emitted from any part of the head portion 130, such as the rear surface 132 of the head portion 130, or from the entirety of the head portion 130.

In embodiments in which the light emitting diodes 206a, 206b generate light across a broad spectral range, generated light may be passed through the light filter 204 in order to spectrally limit light emitted from the head portion 130 of the refill component 100 to a desired spectrum. In embodiments in which the light emitting diodes 206a, 206b generate light in a spectrum that is desired for emission from the refill component 100, then the light filter 204 may be omitted. In certain embodiments, an alternative light guide may be used that is positioned between the light source 202 and the front surface 131 of the head portion 130, without extending beyond the front surface 131, so that light is emitted directly from the front surface 131 of the head portion 130. In such embodiments, it is optional to also use the elastomeric tooth cleaning contacts elements 135b as secondary light guides. In certain embodiments, one or both of the light guide 203 and the light filter 204 may be omitted from the light generating module 200.

In the exemplary embodiment, the refill component 100 also includes electrical contacts 211a, 211b located within the sleeve portion 110, and the electrical contacts 211a, 211b are operably coupled to the light generating module 200 by wires 212a, 212b. The location of the electrical contacts 211a, 211b within the sleeve portion 110 is such that, when the refill component 100 is seated on the stem portion 80 of the handle component 2, electrical contact is made between the electrical contacts 211a, 211b within the sleeve portion 110 and the electrical contacts 94a, 94b of the stem portion 80 of the handle component 2. Electrical contact between the electrical contacts 211a, 211b within the sleeve portion 110 and the electrical contacts 94a, 94b of the stem portion 80 of the handle component 2 serve to provide power to the light generating module 200 from the power source 44 as controlled by the control circuit 50. With power to the light generating module 200 being controlled by the control circuit 50, the control circuit 50 may be configured to provide power to the light generating module 200 based upon user input from the button 3 (see FIG. 1).

As indicated above, the light source may generate light in a broad spectral range, with generated light limited to a narrower spectrum before it is emitted from the refill component 100. The broad spectral range may be generated, for example, by a light source having a single light emitting diode, or by a light source having a plurality of light emitting diodes. In embodiments in which a plurality of light emitting diodes are utilized to generate the broad spectral range, each of the light emitting diodes may emit light in a different spectrum than the other ones of the light emitting diodes, such that the combination of spectrums from the plurality of light emitting diodes combine to create the broad spectral range. In such embodiments, the spectrum of light generated by each light emitting diode may be non-overlapping and/or non-contiguous with the spectrum of light generated by any of the other light emitting diodes. In certain embodiments in which multiple light emitting diodes are utilized as a light source, the spectrum of light emitted from the refill component 100 may be selected by providing power to fewer than all of the plurality of light emitting diodes or by filtering the broad spectral range to select only the desired spectrum to be emitted. Some spectrums of light that may be advantageously emitted by the refill component 100 include a 600 nm to 700 nm wavelength spectrum, a 385 nm to 520 nm wavelength spectrum, and a 200 nm to 300 nm wavelength spectrum. Other spectrums of light may also be emitted from the refill component 100. In certain embodiments, multiple spectrums of light may be emitted simultaneously, with the multiple spectrums being non-overlapping and/or non-contiguous.

Certain wavelength spectrum may be particularly useful. By way of examples, light in the infra-red spectrum can increase blood circulation for gum therapy; light in the blue spectrum can reduce the pain from gum inflammation; light in another area of the blue spectrum can be used to identify bacteria on teeth and gums; light in the UV or purple spectrum can reduce the bacteria in the mouth; and white light can be used to whiten teeth, particularly when associated with light-sensitive chemicals in certain types of toothpaste.

The sleeve portion 110 includes a sleeve cavity 113 that extends along a longitudinal axis A-A from a blind top end 114 to an open bottom end 115 that is located at the proximal end 111 of the sleeve portion 110. The blind top end 114 of the sleeve cavity 113 is blind because it is not visible from the exterior of the refill component 100. The sleeve cavity 113 accommodates the stem portion 80 of the handle component 2 to permit coupling of the refill component 100 to the handle component 2.

The sleeve cavity 113 includes an entry section 171 and an engagement section 172. The entry section 171 of the sleeve cavity 113 has a first minimum diameter and includes the open bottom end 115 of the sleeve cavity 113. The engagement section 172 of the sleeve cavity 113 has a second minimum diameter that is less than the first minimum diameter. In certain embodiments the maximum diameter of the engagement section 172 is less than the minimum diameter of the entry section 171.

The sleeve portion 110 includes an outer surface 119 and an inner surface 173, the inner surface 173 defining the sleeve cavity 113. The inner surface 173 of the sleeve portion 110 includes an annular transverse shoulder 174 located between the entry section 171 of the sleeve cavity 113 and the engagement section 172 of the sleeve cavity 113. The sleeve cavity 113 further includes an uppermost section 175 located between the engagement section 172 and the blind top end 114 of the sleeve cavity 113. As shown, the uppermost section 175 of the sleeve cavity 113 has a transverse cross-sectional area that continually decreases with distance from the engagement section 172 of the sleeve cavity 113 towards the blind top end 114 of the sleeve cavity 113.

The refill component 100 includes a coupling element 140 located near the proximal end 111 of the sleeve portion 110. As shown, the coupling element 140 is an opening formed into the sleeve portion 110 that extends from the open bottom end 115 of the sleeve portion 110 upwardly in the direction of the head portion 130 for a portion of the length of the refill component 100. The coupling element 140 may have a specific structure or shape that permits the coupling element 140 to mate with the coupling element 91 on the stem portion 80 to facilitate coupling and/or locking the refill component 100 to the handle component 2.

The refill component 100 is alterable between a coupled state, as illustrated in FIG. 1, in which the stem portion 80 of the handle component 2 is disposed within the sleeve cavity 113 of the refill component 100, and a decoupled state, in which the refill component 100 is separated from the handle component 2. In the decoupled state, the refill component 100 is separated from the handle component 2. In the coupled state, the refill component 100 is mounted to the handle component 2 and the light generating module 200 is powered by the power source 44 to emit light from the refill component 100.

Figure 5:
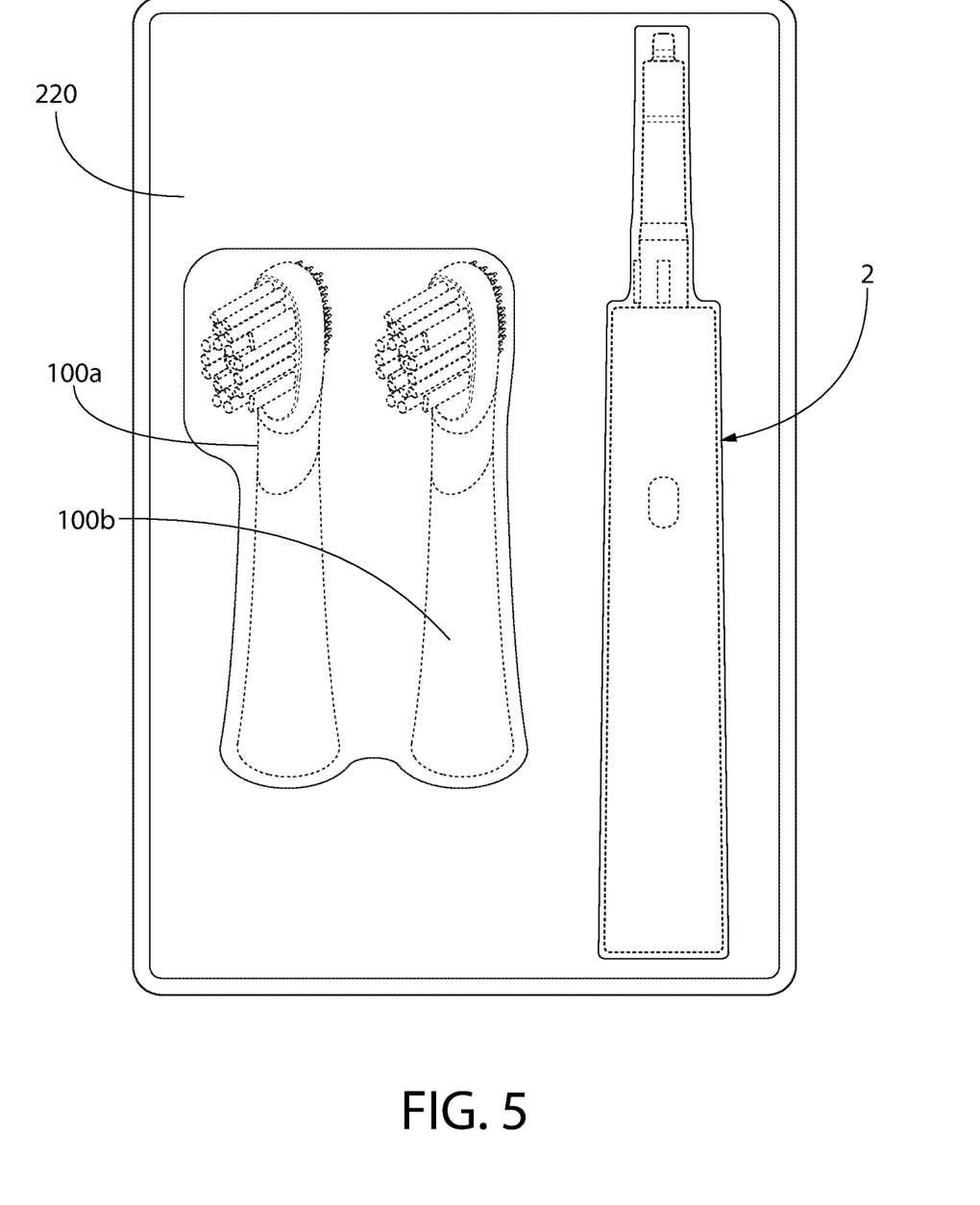
FIG. 5 is a perspective view of an oral care product array including a handle component and a plurality of refill components.

A package 220 is shown in FIG. 5 which contains an oral care product array including one handle component 2, a first refill component 100a, and a second refill component 100b. In certain embodiments, the package 220 may include additional refill components. The handle component 2 may have the features as shown in FIGS. 1 and 2. Each refill component 100a, 100b may have the features as shown in FIGS. 3 and 4. Optionally, each refill component 100a, 100b may have any one or more of the features described for alternative embodiments above. The difference between the refill components 100a, 100b is that the first refill component 100a is configured to emit light in a first spectrum, and the second refill component 100b is configured to emit light in a second spectrum, with the second spectrum being different from the first spectrum. In certain embodiments, the first and second spectrum may be overlapping spectrums. In certain other embodiments, the first and second spectrum may be non-overlapping and non-contiguous spectrums.

Figure 6:
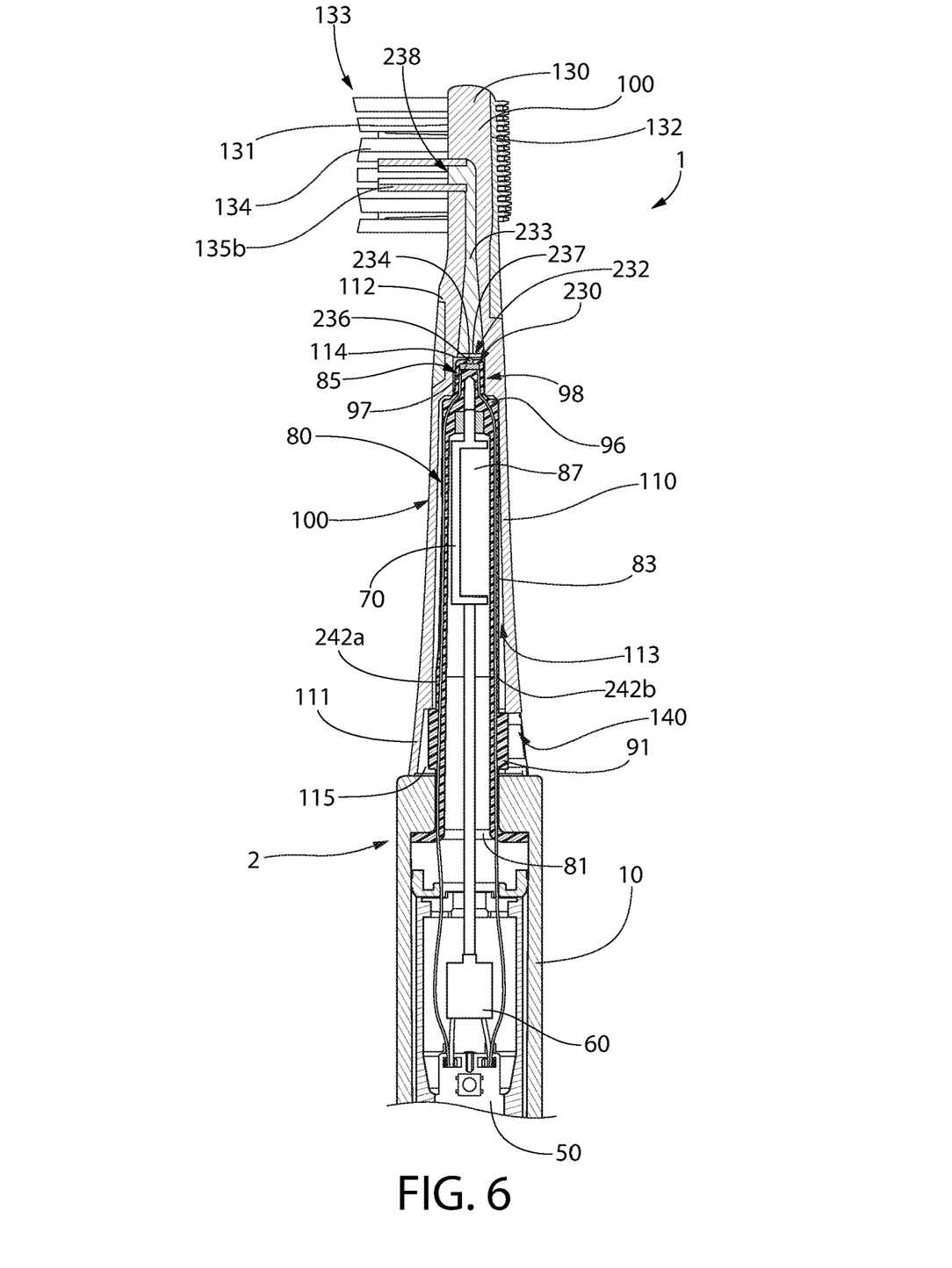
FIG. 6 is a cross-sectional view of an oral care implement having a handle component and a refill component in accordance with another embodiment of the present invention.
Figure 8:
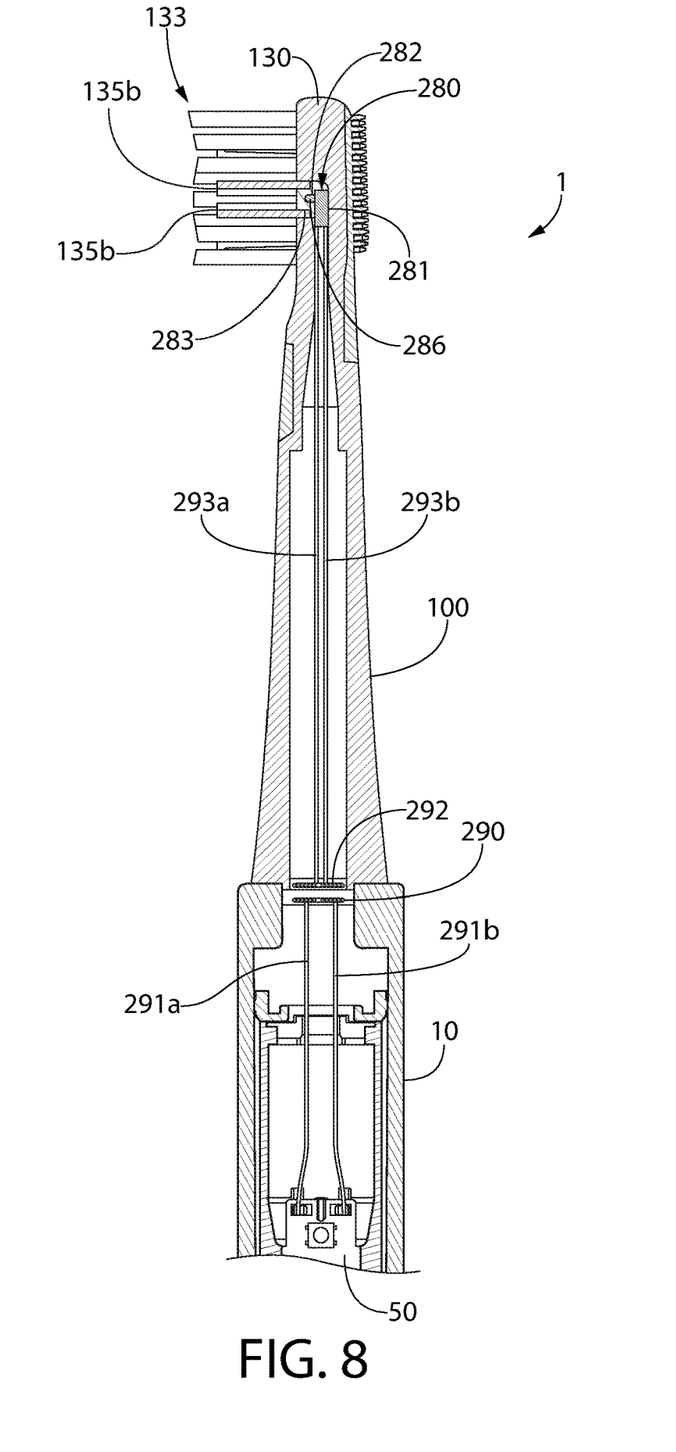
FIG. 8 is a schematic view of an oral care implement having a handle component and a refill component in accordance with still another embodiment of the present invention.

In alternative embodiments, the package may contain refill components 100a, 100b having the features shown for the refill components 100 of FIGS. 6 and 8. Optionally, each refill component 100a, 100b may have any one or more of the features described for alternative embodiments described in conjunction with FIGS. 6 and 8.

In the package 220, each refill component 100a, 100b is shown in the decoupled state. Each refill component 100a, 100b may be separately placed in the coupled state on the handle component 2 (i.e., with the one handle component 2, both refill components 100a, 100b may not be simultaneously placed in the coupled state). When the first refill component 100a is mounted to the handle component 2 in the coupled state, the light generating module of the first refill component 100a is powered by the power source of the handle component 2 to emit light in the first spectrum from the first refill component 100a. Similarly, when the second refill component 100b is mounted to the handle component 2 in the coupled state, the light generating module of the second refill component 100b is powered by the power source of the handle component 2 to emit light in the second spectrum from the second refill component 100b.

An alternative embodiment of an oral care implement 1 is shown in FIG. 6 having a refill component 100 mounted on a handle component 2. The handle component 2 includes most of the same structural features as shown for the handle component 2 of FIGS. 1 and 2. The handle component 2 includes the gripping section 10, a chassis 20, a power source (not shown in FIG. 6), a control circuit 50, a motor 60 having a drive shaft 66, a vibratory source 70, and a stem portion 80.

The stem portion 80 includes an open proximate end 81 which is affixed to the chassis 20 of the gripping section 10 and terminates in a sealed distal end 85. The open proximate end 81 of the stem portion 80 provides a passageway into a stem cavity 87 for receiving and/or retaining the vibratory source 70 and the motor 60 in certain embodiments. The sealed distal end 85 of the stem portion 80 forms an engagement portion 98, which is configured to engage an inner surface of the sleeve portion 110 of the refill component 100 when the refill component 100 is coupled to the handle component 2. The engagement portion 98 includes a stem tip 97 extending from an upper surface 96 of the stem portion 80, such that the upper surface 96 forms an annular transverse shoulder that surrounds the stem tip 97.

A light generating module 230 is located within the handle component 2 at the stem tip 97. The light generating module 230 is configured to emit light across a spectral range, and to that end, the light generating module 230 includes at least one light source 232. As shown, the light generating module 230 includes a light emitting diode 236 as the light source 232. In alternative embodiments, the light generating module 230 may include a plurality of light emitting diodes as the light source 232. The light emitting diode 236 is coupled to the control circuit 50 by lead wires 242a, 242b, so that the control circuit 50 may control power supplied to the light emitting diode 236 from the power source.

The refill component 100 also includes a light guide 233 for guiding light from the light generating module 230 of the handle component 2 to the head portion 130 of the refill component 100. The light guide 233 includes a light receiving end 237, located between the blind top end 114 of the sleeve cavity 113 and the distal end 112 of the sleeve portion 110, and a light emitting end 238, which directs light out of the front surface 131 of the head portion 130. The light emitting end 238 of the light guide 233 also directs light into the elastomeric tooth contact elements 135b, such that the elastomeric tooth contact elements 135b form part of the light emitting end 238 of the light guide 233. A light filter 234 is located at the light receiving end 237 of the light guide 233 to in order to spectrally limit light emitted from the head portion 130 of the refill component 100 to a desired spectrum. In embodiments in which the light emitting diode 236 generates light in a spectrum that is desired for emission from the refill component 100, then the light filter 234 may be omitted.

With the embodiment shown in FIG. 6, the handle component 2 and a plurality of the refill components 100 may be incorporated into an oral care package in the same manner as shown and described for FIG. 5.

Figure 7A:
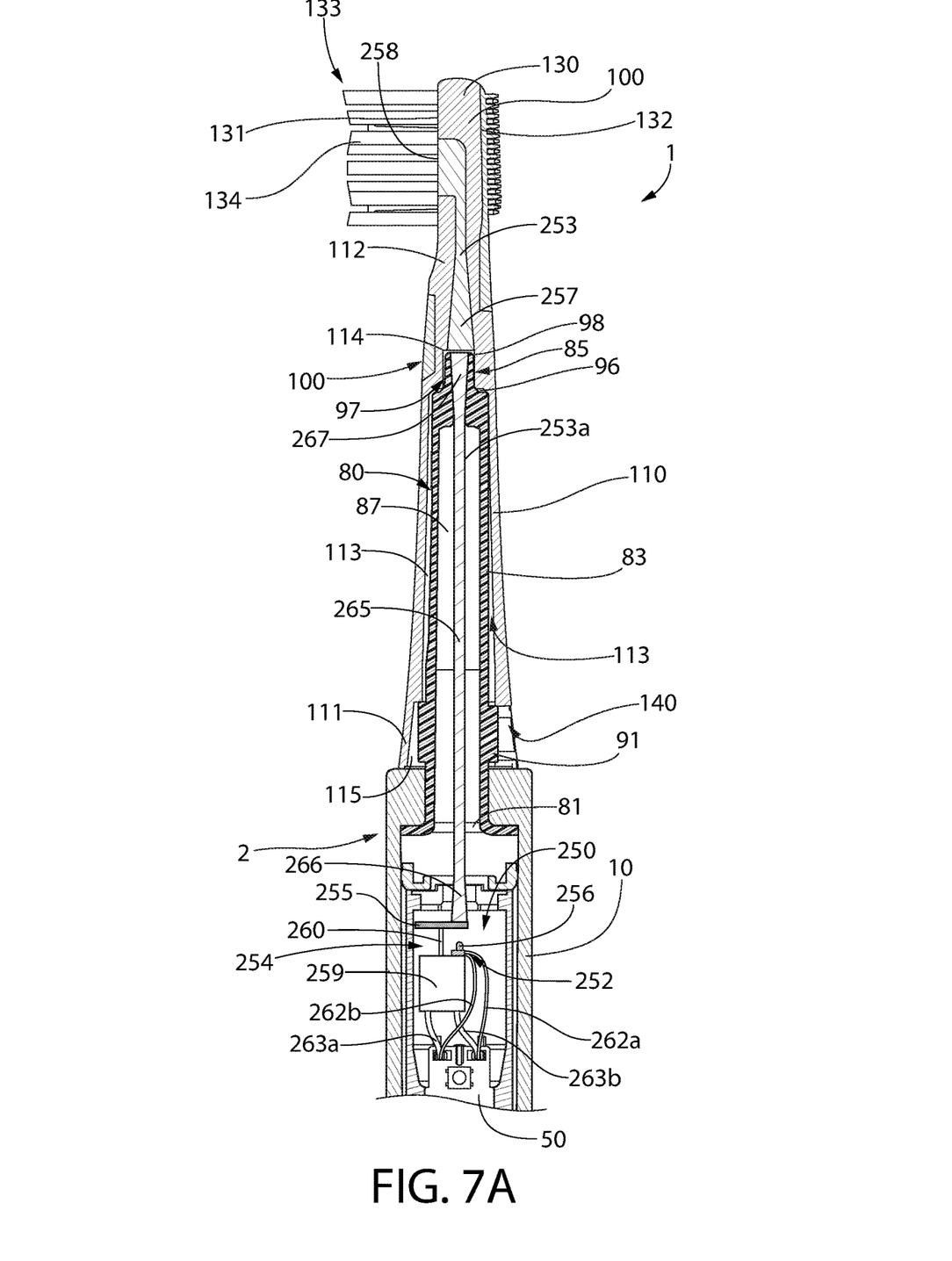
FIG. 7A is a cross-sectional view of an oral care implement having a handle component and a refill component in accordance with still another embodiment of the present invention.

An alternative embodiment of an oral care implement 1 is shown in FIG. 7A having a refill component 100 mounted on a handle component 2. The handle component 2 includes some of the same structural features as shown for the handle component 2 of FIGS. 1 and 2. The handle component 2 includes the gripping section 10, a chassis 20, a power source (not shown in FIG. 7A), a control circuit 50, and a stem portion 80. The handle component 2 of the embodiment depicted does not include a vibratory source 70, however, in alternative embodiments a vibratory source 70 could be included.

The stem portion 80 includes an open proximate end 81 which is affixed to the chassis 20 of the gripping section 10 and terminates in a sealed distal end 85. The open proximate end 81 of the stem portion 80 provides a passageway into a stem cavity 87 for receiving and/or retaining the vibratory source 70 and the motor 60 in certain embodiments. The sealed distal end 85 of the stem portion 80 forms an engagement portion 98, which is configured to engage an inner surface of the sleeve portion 110 of the refill component 100 when the refill component 100 is coupled to the handle component 2. The engagement portion 98 includes a stem tip 97 extending from an upper surface 96 of the stem portion 80, such that the upper surface 96 forms an annular transverse shoulder that surrounds the stem tip 97.

A light generating module 250 is located within the chassis 20 of the handle component 2. The light generating module 250 is configured to emit light in a desired spectrum. To that end, the light generating module 250 includes at least one light source 252 which emits light across a spectral range. As shown, the light generating module 250 includes a light emitting diode 256 as the light source 252. In alternative embodiments, the light generating module 250 may include a plurality of light emitting diodes as the light source 252. The light emitting diode 256 is coupled to the control circuit 50 by lead wires 262a, 262b, so that the control circuit 50 may control power supplied to the light emitting diode 236 from the power source.

Figure 7B:
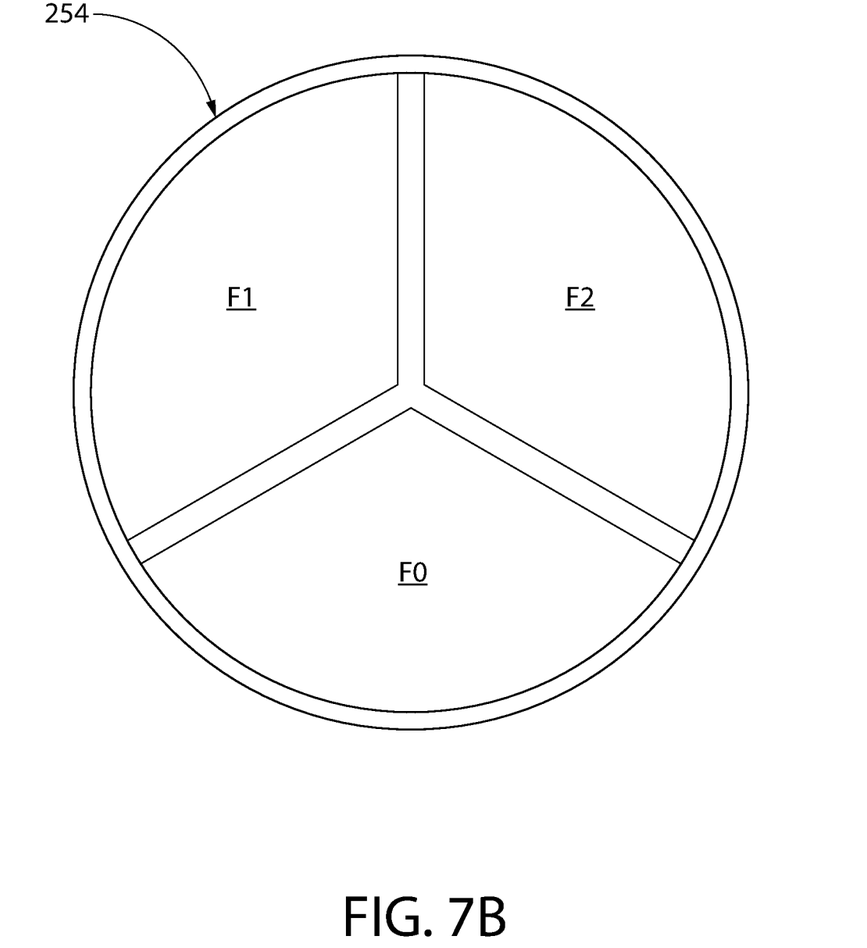
FIG. 7B is a schematic view of a filter plate for the oral care implement of FIG. 7A.

The light generating module 250 includes a light filter module 254. The light filter module 254 includes a plurality of light filters, each of which may be activated, one at a time, with each configured to spectrally limit light generated by the light generating module when activated. The control circuit 50 is operably coupled to a servo motor 259, which is located within the chassis 20 of the handle component 2, through lead wires 263a, 263b. The servo motor 259 is operably coupled to a drive shaft 260, which is in turn operably coupled to a rotatable filter plate 255, which includes the plurality of light filters. The control circuit 50 serves as an actuator for the servo motor 259 and controls rotation of the servo motor 259 to rotate the rotatable filter plate 255. In certain embodiments, the control circuit 50 may be actuated by the actuator button 3 included as part of the handle component 2. FIG. 7B shows a schematic view of the rotatable filter plate 255, which includes three filter sections, F0, F1, and F2. More or fewer light filters may be included as part of the filter plate 255. The handle component 2 includes a light guide 265 having a receiving end 266 positioned to receive light passing through the selected filter (one of F0, F1, or F2) of the rotatable filter plate 255 and guide the received light to the emitting end 267, which directs light out through the stem tip 97 of the stem portion 80. Each filter section, F0, F1, and F2, when activated by optical coupling between the light source 252 and the receiving end 266 of the light guide 265, serves to spectrally limit light generated by the light generating module to the selected spectrum within the spectral range, such that light in the selected spectrum is received by the light guide 265 and emitted at the emitting end 267 of the light guide 265.

The refill component 100 includes a light guide 253 for guiding light from the emitting end 267 of the light guide 265 of the handle component 2 to the head portion 130 of the refill component 100. The light guide 253 includes a light receiving end 257, which is located between the blind top end 114 of the sleeve cavity 113 and the distal end 112 of the sleeve portion 110, and a light emitting end 258, which directs light out of the front surface 131 of the head portion 130. In alternative embodiments, the light emitting end 258 of the light guide 253 may also direct light into one or more elastomeric tooth contact elements which are included as part of the refill component 100.

The broad spectral range may be generated, for example, by a light source having a single light emitting diode, or by a light source having a plurality of light emitting diodes. In embodiments in which a plurality of light emitting diodes are utilized to generate the broad spectral range, each of the light emitting diodes may emit light in a different spectrum than the other ones of the light emitting diodes, such that the combination of spectrums from the multiple light emitting diodes combine to create the broad spectral range. In such embodiments, the spectrum of light generated by each light emitting diode may be non-overlapping and/or non-contiguous with the spectrum of light generated by any of the other light emitting diodes. In certain embodiments in which multiple light sources are utilized, the spectrum of light emitted from the refill component 100 may be selected by providing power to fewer than all of the plurality of light emitting diodes instead of, or in addition to, filtering light from the light source 252 using the light filter module 254.

Yet another alternative embodiment of an oral care implement 1 is shown in FIG. 8 having a refill component 100 mounted on a handle component 2. In the depiction of this embodiment, the features which serve to enable mounting the refill component 100 onto the handle component 2 have been omitted for purposes of simplicity. It is to be understood that the handle component 2 may still include a stem portion 80 and the refill component 100 may still include a sleeve portion 110 for coupling the refill component 100 to the handle component 2. Moreover, features of one or more of the previously discussed embodiments, particularly those which include a light generating module within the refill component 100, may be incorporated into the embodiment of FIG. 8.

The refill component 100 includes a light generating module 280 located within a cavity 281 formed within the head portion 130. The light generating module 280 is configured to emit light in a first spectrum from the refill component 100. To accomplish this, the light generating module 280 includes at least one light source 282 and a light guide 283. In certain embodiments, the light generating module 280 may also include a light filter 204. In the embodiment shown, the light generating module 280 includes a light emitting diode 286 as the light source 282. The light emitting diode 286 is positioned within the cavity 201 to direct light into the elastomeric tooth cleaning contacts elements 135b, both of which serve as part of the light guide 283 for the light generating module 280 to emit light generated by the light source 282 from the refill component 100.

In this embodiment, the handle component 2 includes control circuit 50 which is operably coupled to a handle coil 290 through wire leads 291a, 291b. The handle coil 290 is located within the handle component 2 to be in close proximity to a refill coil 292 located within the refill component 100. Each of the two coils 290, 292 are wire coils, each including several loops of wire to create an electrical inductor. The two coils 290, 292 are in sufficiently close proximity to be inductively coupled, i.e., when the handle coil 290 is powered by the control circuit 50 with an appropriate oscillating power signal, an induction field is established by the handle coil 290, and this induction field is coupled to the refill coil 292 to induce a current to be generated within the refill coil 292. The refill coil 292 is operably coupled to the light generating module 280 through lead wires 293a, 293b, such that the current generated by the inductively coupled refill coil 292 provides power to the light generating module 280.

Figure 9:
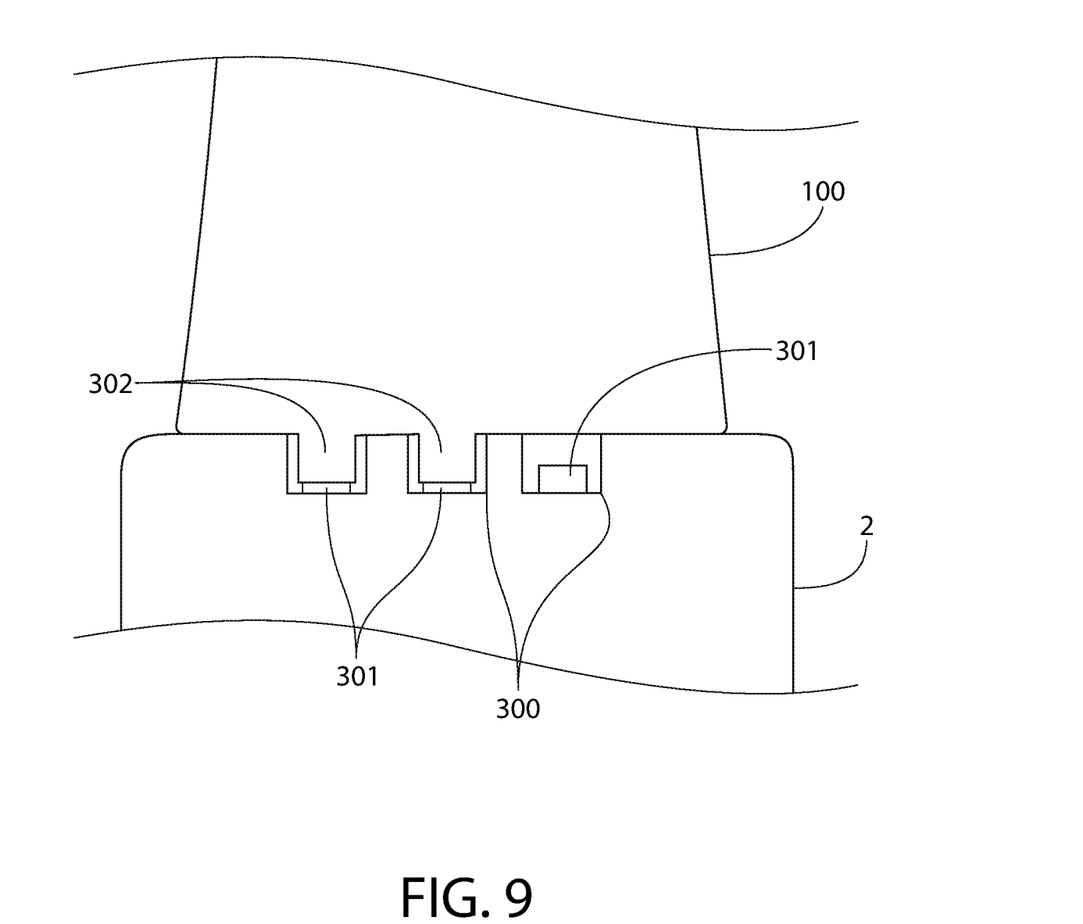
FIG. 9 is a partial schematic view of the handle component and a refill component of an oral care implement in accordance with still another embodiment of the present invention.

Portions of a refill component 100 coupled to a handle component 2 are illustrated in FIG. 9. The combination of the refill component 100 coupled to the handle component 2 provides a selection mechanism which may be used in combination with any of the embodiments described above which may make use of a selection input made to the control circuit 50 to function as an actuator in response to the selection input. As part of the selection mechanism, the refill head 100 includes a plurality of selection indicator features 302, which are shown as a plurality of teeth, and the handle component 2 includes a plurality of selection identifiers 301, which are shown as a plurality of switches. Each selection identifier 301 is located within one of a plurality of receptacles 300, each of which is formed to receive one of the teeth. Each selection identifier 301 is operably coupled to the control circuit 50 within the handle component 2, such that the control circuit 50 may determine which, if any, of the selection identifiers 301 of the handle component 2 are interacting with one of the selection indicator features 302 of the refill component 100 when the refill component 100 is mounted to the handle component 2. By identifying which of the selection identifiers 301 are interacting with one of the selection indicator features 302, the control circuit 50 can identify the type of refill component 100 that has been mounted onto the handle component 2, and use that information as a selection input to determine which of a plurality of light emitting diodes are to be powered and/or which light filter on a rotatable filter plate is to be used to filter a broad spectral range. Such a selection mechanism may also be used for other purposes in connection with an oral care implement when a selection input is required.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care product array comprising:
a handle component comprising a power source and an inductive power circuit operably coupled to the power source and sealed within the handle component;
a first refill component comprising a first light generating module configured to emit light in a first spectrum from the first refill component and a first inductive element operatively coupled to the first light generating module and sealed within the first refill component; and
a second refill component comprising a second light generating module configured to emit light in a second spectrum from the second refill component, the second spectrum being different than the first spectrum, and a second inductive element operatively coupled to the second light generating module and sealed within the second refill component;
the first refill component alterable between: (1) a decoupled state in which the first refill component is separated from the handle component; and (2) a coupled state in which the first refill component is mounted to the handle component and the first light generating module is powered by the power source to emit light in the first spectrum from the first refill component; and
the second refill component alterable between: (1) a decoupled state in which the second refill component is separated from the handle component; and (2) a coupled state in which the second refill component is mounted to the handle component and the second light generating module is powered by the power source to emit light in the second spectrum from the second refill component;

wherein when the first refill component is in the coupled state, the first inductive element is inductively coupled to the inductive power circuit to supply the first light generating module with power from the power source; and wherein when the second refill component is in the coupled state, the second inductive element is inductively coupled to the inductive power circuit to supply the second light generating module with power from the power source.

2. The oral care product array according to claim 1, further comprising a package, each of the handle component, the first refill component, and the second refill component disposed in the package.

3. The oral care product array according to claim 1, wherein:
the handle component comprises a gripping section; and
each of the first and second refill components being a toothbrush refill head comprising a head portion and a plurality of tooth cleaning element extending from a front surface of the head portion.

4. The oral care product array according to claim 3, wherein the handle component further comprises a stem portion extending from a distal end of the gripping section, the stem portion terminating in a sealed distal end; and each of the first and second refill components further comprises a sleeve portion having an inner surface defining a sleeve cavity, the head portion coupled to a distal end of the sleeve portion.

5. The oral care product array according to claim 3, wherein the first light generating module comprises a first light source located in the head portion of the first refill component, and the second light generating module comprises a second light source located in the head portion of the second refill component.

6. The oral care product array according to claim 3, wherein the first light generating module comprises a first light source and a first light guide having a light receiving end and a light emitting end, the light receiving end of the first light guide receiving light from the first light source and the light emitting end of the first light guide emitting light from the head portion of the first refill component, and the second light generating module comprises a second light source and a second light guide having a light receiving end and a light emitting end, the light receiving end of the second light guide receiving light from the second light source and the light emitting end of the second light guide emitting light from the head portion of the second refill component.

7. The oral care product array according to claim 6, wherein for the first refill component, at least one of the plurality of tooth cleaning elements forms a portion of the first light guide and comprises the light emitting end of the first light guide; and wherein for the second refill component, at least one of the plurality of tooth cleaning elements forms a portion of the second light guide and comprises the light emitting end of the second light guide.

8. The oral care product array according to claim 5, wherein the first light generating module further comprises a first light filter that spectrally limits light generated by the first light source and emitted from the first refill component to the first spectrum; and wherein the second light generating module further comprises a second light filter that spectrally limits light generated by the second light source and emitted from the second refill component to the second spectrum.

9. An oral care implement comprising:
a handle component comprising:
a gripping section;
a power source; and
an inductive power circuit operably coupled to the power source; and
a toothbrush refill head comprising:
a head portion;
a plurality of tooth cleaning elements extending from a front surface of the head portion;
a light generating module configured to generate light across a spectral range; and
an inductive element operably coupled to the light generating module;
the toothbrush refill head alterable between: (1) a decoupled state in which the toothbrush refill head is separated from the handle component; and (2) a coupled state in which the toothbrush refill head is mounted to the handle component and the inductive element of the toothbrush refill head is inductively coupled to the inductive power circuit of the handle component to supply power from the power source to the light generating module.

10. The oral care implement according to claim 9, wherein the handle component further comprises a stem portion extending from a distal end of the gripping section, the stem portion terminating in a sealed distal end; and wherein the toothbrush refill head further comprises a sleeve portion having an inner surface defining a sleeve cavity, the head portion coupled to a distal end of the sleeve portion.

11. The oral care implement according to claim 9, wherein the light generating module comprises a light source located in the head portion of the toothbrush refill head.

12. The oral care implement according to claim 11, wherein the light generating module further comprises a light guide having a light receiving end and a light emitting end, the light receiving end receiving light from the light source and the light emitting end emitting light from the head portion of the toothbrush refill head, wherein at least one of the plurality of tooth cleaning elements forms a portion of the light guide and comprises the light emitting end of the light guide.

13. The oral care implement according to claim 11, wherein the light generating module further comprises a light filter that spectrally limits light generated by the light source and emitted from the toothbrush refill head to the spectral range.

* * * * *